US010098606B2

United States Patent
Star-Lack et al.

(10) Patent No.: US 10,098,606 B2
(45) Date of Patent: Oct. 16, 2018

(54) AUTOMATIC ORGAN-DOSE-ESTIMATION FOR PATIENT-SPECIFIC COMPUTED TOMOGRAPHY SCANS

(71) Applicant: VARIAN MEDICAL SYSTEMS, INC., Palo Alto, CA (US)

(72) Inventors: Josh Star-Lack, Palo Alto, CA (US); Adam Wang, Menlo Park, CA (US); Alexander Maslowski, Lexington, KY (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 60 days.

(21) Appl. No.: 15/055,647

(22) Filed: Feb. 29, 2016

(65) Prior Publication Data

US 2017/0245825 A1    Aug. 31, 2017

(51) Int. Cl.
| | |
|---|---|
| *G06K 9/00* | (2006.01) |
| *A61B 6/00* | (2006.01) |
| *A61B 6/03* | (2006.01) |
| *G06T 7/00* | (2017.01) |

(52) U.S. Cl.
CPC ............. *A61B 6/542* (2013.01); *A61B 6/032* (2013.01); *G06T 7/0012* (2013.01); *G06T 7/0081* (2013.01); *G06T 2207/10081* (2013.01)

(58) Field of Classification Search
CPC ..................... A61B 6/542; G06T 2207/10081
See application file for complete search history.

(56) References Cited

U.S. PATENT DOCUMENTS

| | | | |
|---|---|---|---|
| 2008/0292055 A1* | 11/2008 | Boone | G01T 1/02 378/97 |
| 2017/0091574 A1* | 3/2017 | Udupa | G06K 9/4638 |
| 2017/0213339 A1* | 7/2017 | Hibbard | G06T 7/0012 |

* cited by examiner

*Primary Examiner* — Oneal R Mistry
(74) *Attorney, Agent, or Firm* — Su IP Consulting

(57) ABSTRACT

In accordance with at least some embodiments of the present disclosure, a process for calculating patient-specific organ dose is presented. The process may include constructing a computed tomography (CT) volume based on CT images generated by a CT scanner. The process may include segmenting the CT volume into a plurality of organ regions, generating a material density map for the CT volume based on Hounsfield Unit (HU) values, and generating a dose distribution map for the CT volume based on the material density map by simulating particles emitting from the CT scanner and flowing through the CT volume. The process may further generate a dose value delivered to a specific organ region of the plurality of organ regions based on the dose distribution map.

22 Claims, 7 Drawing Sheets

CT Volume
(310)

Lung
Expert Case
(321)

Atlas
(320)

Organ Region
for Lung
(331)

Segmented Volume
(330)

Boltzmann Transport Equation
(510)

Segmented Volume
(520)

Dose Distribution Map
(530)

US 10,098,606 B2

AUTOMATIC ORGAN-DOSE-ESTIMATION FOR PATIENT-SPECIFIC COMPUTED TOMOGRAPHY SCANS

BACKGROUND OF THE DISCLOSURE

Field of the Disclosure

Embodiments of the present disclosure relate generally to rapid, accurate and fully automated system and method to estimate patient-specific radiation doses from computed tomography scans.

Description of the Related Art

Unless otherwise indicated herein, the approaches described in this section are not prior art to the claims in this application and are not admitted to be prior art by inclusion in this section.

Although Computed Tomography (CT) is a widely used imaging technique, CT radiation dose is a growing public health concern. Current dose reporting metrics such as the Computed Tomography Dose Index (CTDI) or Dose-Length Product (DLP) are measured using a uniform acrylic cylinder and represent dose to the cylinder, rather than dose to the actual patient. Thus, these dose monitoring metrics are not a good indication of the dose amount to the organs of an actual patient.

DETAILED DESCRIPTION

Figure 1:
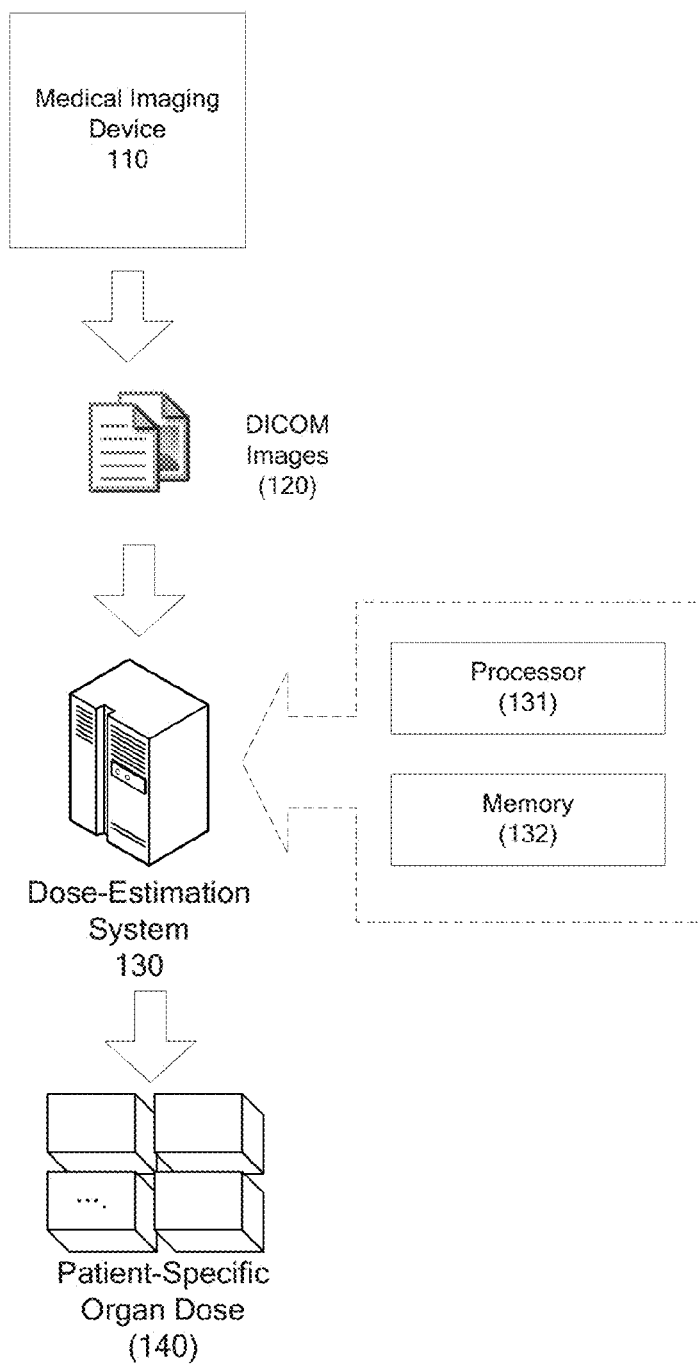
FIG. 1 shows a block diagram illustrating one embodiment of a system configured La provide automatic patient-specific CT dose-estimation.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated herein.

The present disclosure is related to systems and methods to automatically estimate CT radiation doses delivered by CT scans to a patient's organ. Specifically, a dose-estimation system may be configured with an auto-segmentation module to automatically determine specific organ boundaries and delineate organs of interest. The dose-estimation system may be configured with a dose-distribution-calculation module to model CT scanner, and generate a spatially-dependent dose distribution map by solving a Boltzmann Transport Equation (BTE) using finite-element methods. The dose-estimation system may further be configured with a dose-tabulation module for computation of individual organ doses based on the dose distribution map.

FIG. 1 shows a block diagram illustrating one embodiment of a system configured to provide automatic patient-specific CT dose-estimation. In FIG. 1, a medical imaging device 110 may perform a CT scan operation on a patient, and generate a set of Digital Imaging and Communications in Medicine (DICOM) images 120 associated with the patient. A dose-estimation system 130 may take the DICOM images 120 as inputs, and generate a patient-specific organ dose 140 for one of the patient's organs (organ-of-interest). The patient-specific organ dose 140 may be used to show how much radiation the patent's organ-of-interest was exposed to during the CT scan operation.

Examples of the medical imaging device 110 may include, without limitation, X-ray device, CT device, cone-beam CT device, and others. The medical imaging device 110 may have a "radiation source" for emitting cone-beam, pencil-beam, and/or fan-beam particles (e.g., photons and electrons). The medical imaging device 110 may further have a "detector panel" for receiving the particles emitted from the radiation source and passed through a "scanning object" (e.g., a patient) placed between the radiation source and the detector panel. The emitted particles may be generated inside a spectrum ranging from 0 keV to 150 keV, and may interact with the scanning object through photo-electric absorptions, Rayleigh (or coherent) scattering, and Compton (or incoherent) scattering. When the diagnostic energy spectrum is lower than 150 keV, scattered electrons travel a negligible distance. Thus, the present disclosure only evaluates the radiation effect of photons being transported by the medical imaging device 110.

During one CT scanning interrogation, the medical imaging device 110 may project photons towards the detector panel at a particular angle/direction, and generate a DICOM image 120 based on the photons detected by the detector panel. Afterward, the radiation source-detector panel (source-detector pair) may be rotated to a different angle/direction, and perform another round of CT scanning interrogation of the scanning object to generate additional DICOM image 120. Throughout the disclosure, the terms "image", "projection", and "DICOM image" are used interchangeably to broadly refer to 2-dimension (2D) medical data generated from a single CT scanning interrogation. Thus, a CT scanning operation may include multiple CT scanning interrogations from multiple angles/directions, and may generate a set of DICOM images 120.

In some embodiments, the dose-estimation system 130 may provide an interface to a user for uploading a patient's DICOM images 120 obtained from a CT scanning operation. The user may also use the interface to input into the dose-estimation system 130 various information associated with the DICOM images 120, such as the suitable attributes (e.g., sex, age, height, etc) of the patient, the appropriate scan protocol (e.g., chest scan), the CT scanner's model (e.g., GE Lightspeed), the bowtie filter type used (e.g., head or body), the beam collimation width of the CT scanner, and the peak kilo-voltage (kVp) applied by the CT scanner. The user may also indicate the patient's organ-of-interest, and the dose-estimation system 130 may generate a patient-specific organ dose 140 to show how much radiation the particular organ-of-interest was exposed to during the CT scan operation.

In some embodiments, the dose-estimation system 130 may include one or more processors 131, memory 132, and/or other components, so that it could process the DICOM images 120 and generate the patient-specific organ dose 140. In some embodiments, the processor(s) 131 may include central processing units (CPUs) for controlling the overall operation of the dose-estimation system 130. The processor(s) 131 may accomplish this by executing software or firmware stored in memory 132. The processor(s) 131 may be or may include, one or more programmable general-purpose or special-purpose microprocessors, digital signal processors (DSPs), programmable controllers, application specific integrated circuits (ASICs), programmable logic devices (PLDs), graphical processing units (GPUs) or the like, or a combination of such devices. The memory 132 may represent any form of random access memory (RAM), read-only memory (ROM), flash memory (as discussed above), or the like, or a combination of such devices. In use, the memory 132 may contain, among other things, a set of machine readable instructions which, when executed by the processor 131, causing the processor 131 to perform at least some embodiments of the present disclosure.

Figure 2:
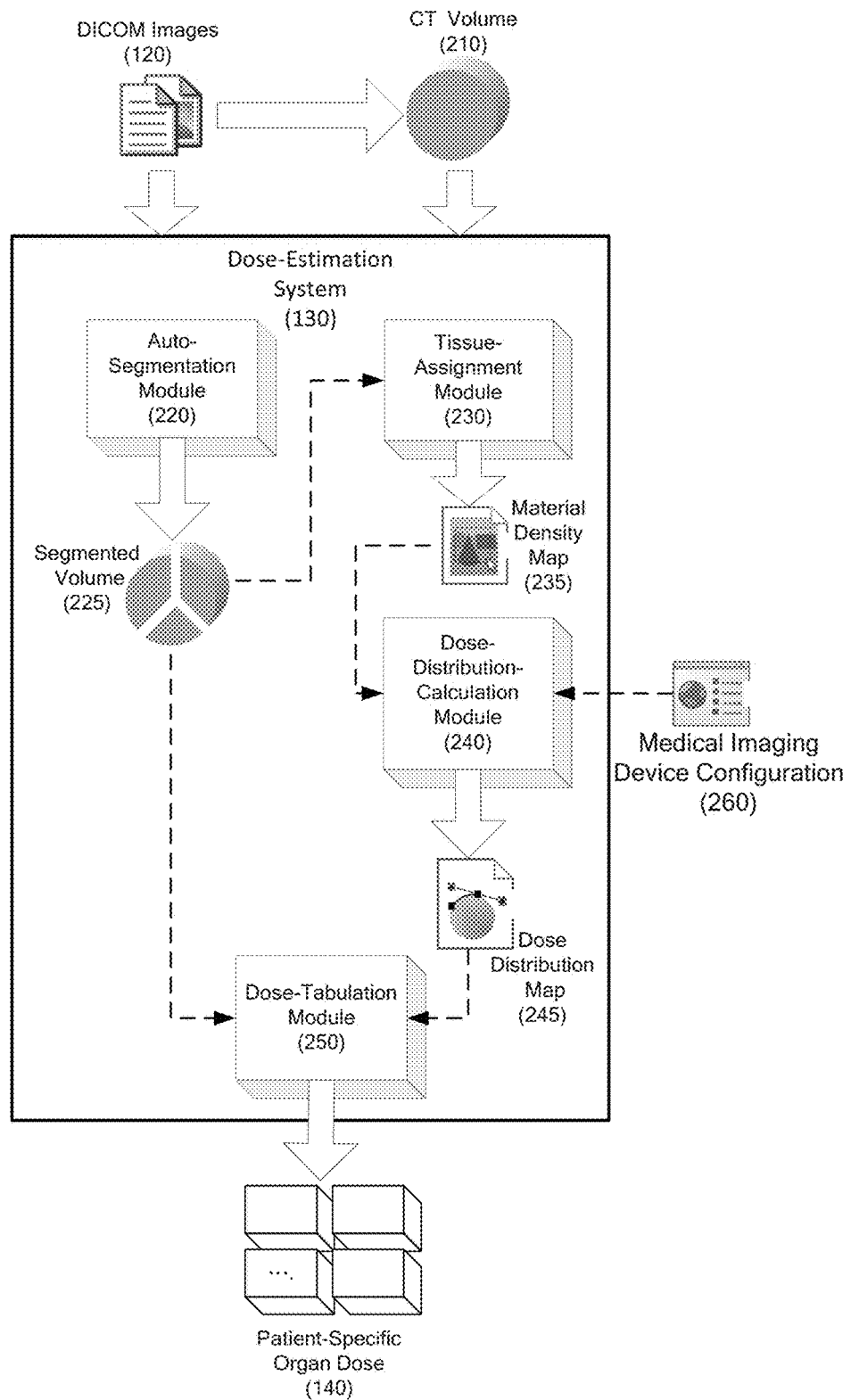
FIG. 2 illustrates one embodiment of a dose-estimation system for estimating patient-specific organ dose.

FIG. 2 illustrates one embodiment of a dose-estimation system for estimating patient-specific organ dose. In FIG. 2, the dose-estimation system 130 may be configured to generate patient-specific organ dose 140 based on a configuration 260 of a medical imaging device and a set of DICOM images 120 originated from the medical imaging device. The dose-estimation system 130 may contain, among other elements, an auto-segmentation module 220, a tissue-assignment module 230, a dose-distribution-calculation module 240, and a dose-tabulation module 250. The modules contained in the dose-estimation system 130 may be implemented either as hardware components, or software applications running on a suitable computer. Further, some of the above modules may be combined into a single module, or a single module may be divided into additional sub-modules not shown in FIG. 2.

In some embodiments, the dose-estimation system 130 may first convert the DICOM images 120 into a CT volume 210, which may be used to show in three-dimensional (3D) the distribution of materials inside the scanning object. Throughout the disclosure, the terms "volume", "3D volume", and "CT volume" are used interchangeably to broadly refer to 3D medical data reconstructed based on a set of DICOM images. For example, a 3D CT volume of a patient's heart may be reconstructed based on a set of 2D DICOM images or 2D projections taken by a CT scanner through the patient's heart and its surrounding anatomy.

In some embodiments, the dose-estimation system 130 may further discretize/partition the CT volume 210 into a set of 3D cells (or "voxels"). A voxel represents a value on a fixed and regular grid in 3D space and may correspond to any number of 3D structures, such as, without limitation, cubes, hexagonal structures having two hexagons as bases and six rectangular sides, with the lengths of all edges being identical, or structures in any isotropic shapes and sizes. Afterward, the dose-estimation system 130 may transfer the CT volume 210 having discretized voxels to the auto-segmentation module 220 for further processing.

In some embodiments, the auto-segmentation module 220 may be configured to automatically segment the CT volume 210 into a segmented volume 225 having one or more organ regions. Each "organ region" may have delineated boundaries in the segmented volume 225, representing an area in the CT volume 210 that is associated with a patient's organ or body structure. The segmented organ regions may correspond to a patient's anatomical parts such as breasts, lungs, heart, stomach, liver, pancreas, spleen, kidneys, colon, small intestine, bladder, gonads, uterus/cervix (female), prostate (male), skeletal bone, bone marrow, and skin, etc. After auto-segmentation, each of the segmented organ regions may be associated with a subset of the voxels in the CT volume 210.

In some embodiments, the auto-segmentation module 220 may use a combination of feature-based and atlas-based methods to perform its segmentation operations. Specifically, the auto-segmentation module 220 may first use the feature-based approach to segment those organ regions (such as bones, lungs, and eyes) that have distinctive image features. Afterward, the auto-segmentation module 220 may use the atlas-based approach to segment the remaining organ regions. When the atlas-based outcome does not align with the CT volume 210, the auto-segmentation module 220 may perform deformable registration to further adjust the auto-segmentation operations based on the patient's actual anatomy represented in the CT volume 210.

In some embodiments, the auto-segmentation module 220 may perform the feature-based segmentation operation based on the image density Hounsfield Unit (HU) values presented in the CT volume 210. Specifically, the auto-segmentation module 220 may evaluate the HU gradient of the voxels in CT volume 210. Using previously-defined HU value thresholds and density ranges, the auto-segmentation module 220 may identify structures in the CT volume 210 that have distinctive features. Each identified structure may then be classified, based on its respective HU values, to either non-organ materials (such as air, water), or organ regions (such as lung, adipose, soft-tissue, muscle or bone).

Figure 3:
FIG. 3 illustrates an atlas-based automatic segmentation scenario.
Figure 3:
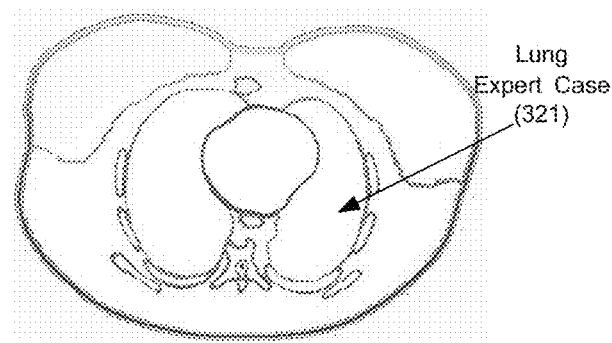
Figure 3:
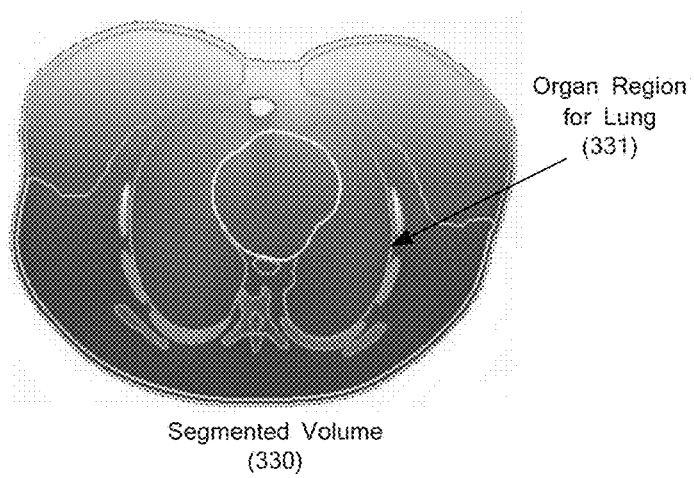

FIG. 3 illustrates an atlas-based automatic segmentation scenario, according to some embodiments of the present disclosure. In FIG. 3, the auto-segmentation module 220 of FIG. 2 may perform automatic segmentation on a CT volume 310 by using an atlas 320. Specifically, the "atlas" may refer to a library of expert cases. Each "expert case" may contain a set of CT volumes previously classified by body regions (e.g., chest, abdomen, and/or pelvis) and having organs-of-interest (e.g., breasts, lungs, heart, liver, stomach, colon, gonads) being segmented with a high degree of accuracy. Thus, in addition to the feature-based auto-segmentation, the auto-segmentation module 220 may perform the atlas-based auto-segmentation by selecting an atlas 320 that substantially matches the CT volume 310, and dissecting the structures and organ regions from the CT volume 310 using the expert cases contained in the atlas 320.

In FIG. 3, the auto-segmentation module 220 may treat the CT volume 310 as a "current case" and try to spatially align ("register") the contour of the expert cases in the atlas 320 with the HU gradient associated with the voxels of the CT volume 310. The segmented volume 330 may be added as an expert case into the atlas 320 for future usage.

In some embodiments, the auto-segmentation module 220 may be configured to detect specific tumor regions in the CT volume 310 based on a tumor atlas. The tumor atlas may contain a library of tumor expert cases. The multiple tumor expert cases in the tumor atlas may be sorted by specific tumor regions, such as head and neck, thorax, breast, gynecological, male and female pelvic, or be sorted within each anatomy group based on the tumor, nodal, and metastasis staging (TNM-staging) with multiple staging combinations.

In some embodiments, because the accuracy of single-atlas auto-segmentations may vary from atlas to atlas, the auto-segmentation module 220 may apply multiple atlases to a single patient's CT volume 310. Expert cases from the multiple atlases may be individually registered to the current case, and the individual segmentations will then be fused into a combined segmentation, for example by using the Simultaneous Truth and Performance Level Estimation (STAPLE) algorithm. The STAPLE fusion contour better approximates the true segmentation by minimizing the variations among the single-atlas segmentations, effectively averaging out any errors, and is capable of weighting each of the individual segmentations based on its estimated accuracy. The multi-atlas approach is not expected to significantly increase run time since the individual segmentations can be performed in parallel.

In some embodiments, because the CT volume 310 and the atlas 320 are coming from different patients, the expert cases in the atlas 320 may not align perfectly with the CT volume 310. In this case, the auto-segmentation module 220 may perform a "deformable registration" process to match the anatomy of the current case with the expert cases as closely as possible. Specifically, after finding a best-matching expert case (e.g., lung expert case 321) from the atlas 320 for the CT volume 310 based on patient's age, gender, weight, and exam type, the auto-segmentation module 220 may be configured to deformably register the best-matching expert case to the current case using a variation of the demons registration algorithm, including a multi-resolution pyramid which can increase convergence speed and improve robustness to image distortions.

In some embodiments, the demons registration algorithm may use gradient information derived from voxels in the CT volume 310 to calculate a demons force required to deform the best-matching expert case onto the current case. The auto-segmentation module 220 may use an optical flow equation to iteratively calculate the demons force as voxel displacement vectors. The voxel displacement vectors may then be regularized with the Gaussian function, and used to propagate the best-matching expert case's organ boundaries onto the current case, thereby refining the organ boundaries for the current case. Such auto-segmentation approach may be sufficiently accurate to provide organ dose-estimations since random errors at the organ boundaries may be averaged out when computing the total organ dose.

In some embodiments, after completing the above auto-segmentation operations, the auto-segmentation module 220 may generate a segmented volume 330 for the CT volume 310. The segmented volume 330 may include a set of identified organ regions, each of which contains a subset of voxels selected from the voxels in the CT volume 310. For example, the segmented volume 330 may contain an organ region for lung 331, and the organ region for lung 331 may be defined by a subset of voxels located inside the contoured boundaries of the lung in the segmented volume 330. The segmented volume 330 corresponds to the segmented volume 225 of FIG. 2.

Referring back to FIG. 2, after the auto-segmentation operation, the dose-estimation system 130 may utilize the tissue-assignment module 230 to create a material density map 235 for the segmented volume 225. Specifically, the "material density map" may contain a corresponding material type and a density for each voxel in the segmented volume 225. In some embodiments, the tissue-assignment module 230 may automatically assign a material type and density to a voxel based on the voxels' HU value stored in the segmented volume 225. The material types may include biological material types such as water, bone, lung, air, adipose, muscle, soft tissue, bone marrow, as well as non-biological material types such as iodine (accounting for contrast agent) and carbon fiber (accounting for the patient table which shields the patient when the radiation source is below the table).

In some embodiments, the tissue-assignment module 230 may assign a voxel's material type based on a linear-combination of multiple materials (e.g., water, bone). Afterward, the tissue-assignment module 230 may determine a density value for the voxel based on the voxel's material type or the linear-combination of multiple materials. The density value may also determine the voxel's x-ray attenuation and scattering properties. The tissue-assignment module 230 may generate the material density map 235 based on the material type and density determined for each of the voxels in the segmented volume 225.

In some embodiments, the dose-distribution-calculation module 240 may generate a dose distribution map 245 associated with the segmented volume 225, based on the material density map 235 provided by the tissue-assignment module 230 and a set of medical imaging device configuration 260. Specifically, the dose-distribution-calculation module 240 may simulate a medical imaging device based on the medical imaging device configuration 260; and simulate such medical imaging device performing a CT scanning operation on the organ regions of the segmented volume 255, based on the organ regions' material types and densities stored in the material density map 235. During the simulations, the dose-distribution-calculation module 240 may estimate the radiation doses caused by the photons flowing through the segmented volume 255 and experienced by the voxels in the segmented volume 255. The estimated distribution of radiation dose (e.g., photon fluence) among the voxels may be stored in a dose distribution map 245, which may subsequently be used to calculate the patient-specific organ dose 140.

Figure 4:
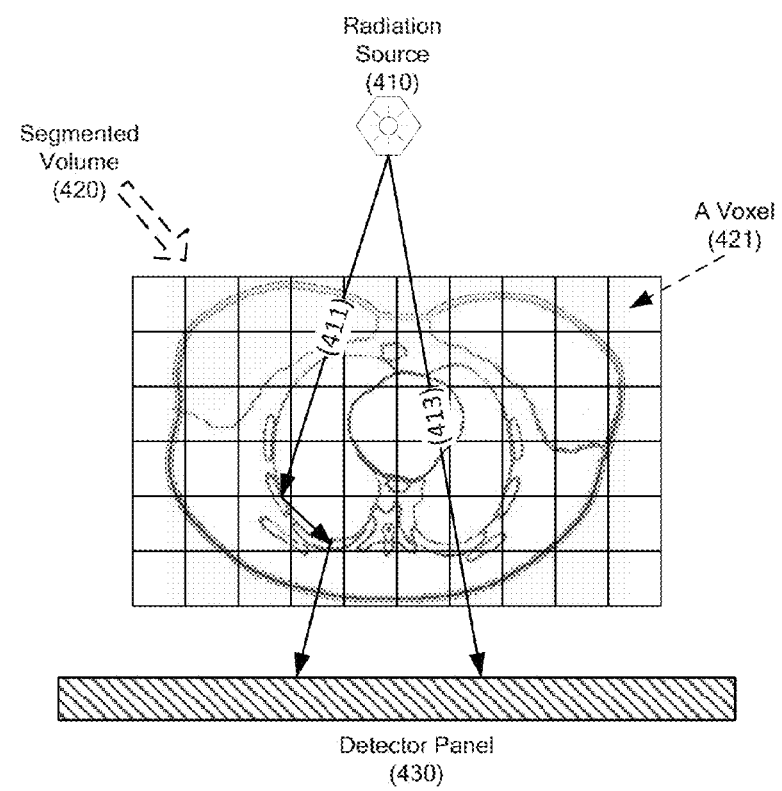
FIG. 4 illustrates a dose-estimation system configured to simulate a medical imaging device performing a clinical CT scanning operation on a patient.
Figure 4:
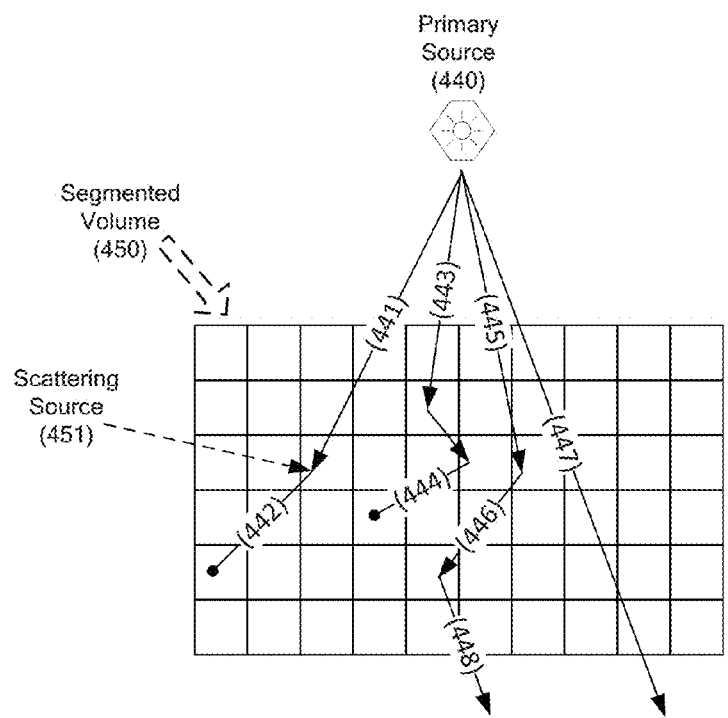

FIG. 4 illustrates a dose-estimation system configured to simulate a medical imaging device performing a clinical CT scanning operation on a patient, in accordance with certain embodiments of the present disclosure. Assuming the segmented volume 420 is constructed based on DICOM images generated by a CT scanner having a radiation source 410 and a detector panel 430, the dose-distribution-calculation module 240 of FIG. 2 may be configured to simulate such CT scanner performing a similar CT scanning operation on the patient.

In some embodiments, the dose-distribution-calculation module 240 may utilize the medical imaging device configuration 260 for accurate modeling of the medical imaging device used in clinical CT scanning operation. The medical imaging device configuration 260 may be stored in a modulated XML format file, and may be easily-adjustable to accommodate a diverse range of different medical imaging devices. Some of the medical imaging device configurations 260 may be obtained from the header files of the DICOM images, while others may be inputted by users through an interface of the dose-estimation system 130. The medical imaging device configuration 260 for a CT scanner may include parameters such as Scanner Model, kV, Exposure, Scan Range, Longitudinal Coverage, Helical Pitch, Helical Start Angle, Noise Index, Slice Thickness, Bowtie Filter, CTDIvol, DLP, etc.

As shown by the top-half of FIG. 4, based on the medical imaging device configuration 260, the dose-distribution-calculation module 240 may construct a simulation framework, including a simulated CT scanner having the radiation source 410 and the detector panel 430, and including the organ regions identified in the segmented volume 420. Based on this simulation framework, the dose-distribution-calculation module 240 may simulate photons emitting from the radiation source 410 along a source trajectory, and passing through the organ regions via travel paths 411 and 413 before reaching the detector panel 430.

In some embodiments, the dose-distribution-calculation module 240 may simulate the anisotropy of the radiation source 410 by using a 2D fluence grid, which provides a phase-space description of spatially-dependent particle fluence and energy spectra. Such an approach allows the simulating of relevant hardware aspects of the CT scanner, including kVp (modifies the beam spectrum), tube current modulation (scales the fluence), bowtie filter and heel effect (affect fluence and energy spectra), and position-dependent collimation including over-ranging protection (determines spatial masking of the fluence grid). This approach may also allow this collection of radiation sources 410 to be specified for each CT scan operation and will account for various scanner-specific outputs.

As shown by the bottom-half of the FIG. 4, the dose-distribution-calculation module 240 may simulate a beam of photons emitting from the radiation source 440 (primary source) of a CT scanner and passing through the segmented volume 450 via traveling paths 441, 443, 445, and 447. This beam of photons may be referred to as a "primary beam." During the first iteration of simulation, the dose-distribution-calculation module 240 may ray-trace the primary beam's traveling paths, and simulate the photons of the primary beam passing, being scattered, or being absorbed among the voxels of the segmented volume 450. In FIG. 4's example, a photon indicated by traveling path 441 may scatter in one of the voxels in the segmented volume 450. The dose-distribution-calculation module 240 may treat the location of the scattering as a scattering source 451, from which the photon embarks on a new traveling path 442 at the same or lower energy. During the first iteration of simulation, the dose-distribution-calculation module 240 may collect all the scattering sources instigated by photons from the primary beam, and consider these scattering sources as "first iteration scattering sources."

In a second iteration of simulation, the dose-distribution-calculation module 240 may simulate the transporting of the photons from the first iteration scattering sources to nearby voxels. Some of the photons may be absorbed by the nearby voxels (as shown by travel paths 442 and 444), while other photons may scatter to other directions (as shown by travel path 446), thereby creating new scattering sources (second iteration scatter sources). In a subsequent iteration of simulation, the dose-distribution-calculation module 240 may simulate the photons traveling from the second iteration scattering sources to nearby voxels, and update the scattering sources for the next iteration. The dose-distribution-calculation module 240 may perform additional iterations of the above simulation operations until convergence (arriving at a solution that is close to the exact solution within some pre-specified error tolerance, e.g., 0.001%), which is sufficient to simulate the majority (e.g., 99.999%) of the radiation energies accumulated in a patient's body during an actual CT scanning operation.

During the above multiple iterations of simulation, the dose-distribution-calculation module 240 may monitor those voxels in the segmented volume 450 that are affected by the ray-tracing of photons, and examine the angular profiles and the energy magnitudes of these photons. Since the behaviours of the photons emitting from the primary source 440 may be determined by the angular profiles and the energy magnitudes of the CT scanner which produces these photons, the medical imaging device configuration 260 associated with the CT scanner may be used to provide such angular profiles and energy magnitudes. Likewise, how the photons may be scattered or absorbed in the voxels, as well as how the voxels may affect the energies and behaviours of the photons, may be dictated by the material types and density values defined in the material density map 235 which is provided by the tissue-assignment module 230.

In some embodiments, the dose-distribution-calculation module 240 may utilize a Boltzmann Transport Equation (BTE), which is capable of describing the macroscopic behaviours of the particles (e.g., photons with certain angular profiles and energy magnitudes) flowing through an object (e.g., voxels having certain material types and densities), to follow the above multiple iterations of estimations. The BTE may then be solved to provide a solution showing the distribution of the photon fluence among the voxels in the segmented volume 450.

Figure 5:
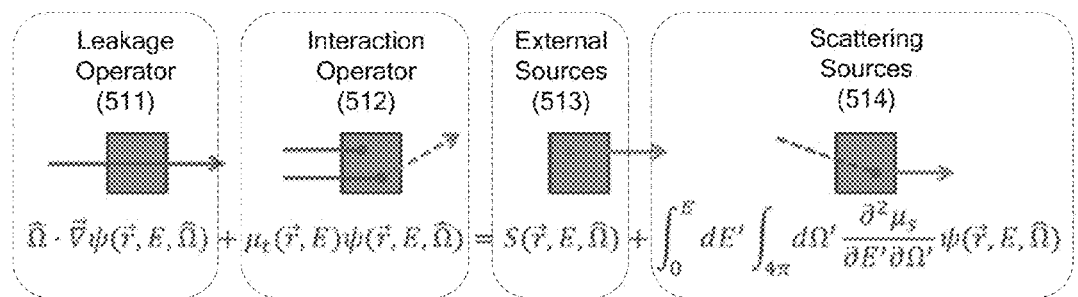
FIG. 5 illustrates using BTE to calculate dose distributions during a simulated CT scanning operation and generate a dose distribution map.
Figure 5:
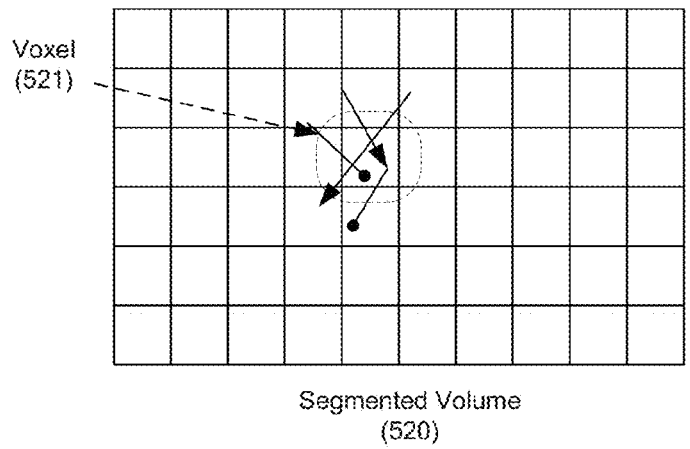
Figure 5:
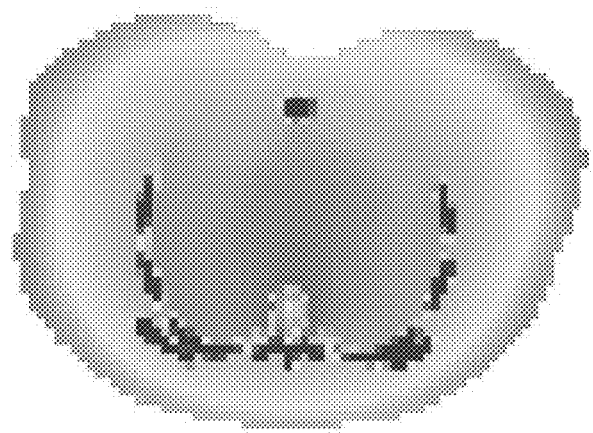

FIG. 5 illustrates using BTE to calculate dose distributions during a simulated CT scanning operation and generate a dose distribution map, in accordance with certain embodiments of the present disclosure. In some embodiments, the dose-distribution-calculation module 240 of FIG. 2 may utilize a BTE 510 to record the above multiple iterations of simulation. The BTE 510 is a differential equation that governs the primary and scattering behaviours of photons, and can be numerically solved by discretizing phase-space (spatial location, energy, and/or angle) and applying a deterministic finite element algorithm. The discretization in space may be done using finite elements, the discretization in energy may be done using energy groups, and the discretization in angle may be done using discrete ordinates. The solution of the BTE 510 may be used to show the distribution of photon fluence across the voxels of the segmented volume.

In FIG. 5, the BTE 510 has two items on the left of its equation: leakage operator 511 and interaction operator 512; and two items on the right of its equation: external sources 513 and scattering sources 514. In other words, the sum of the leakage operator 511 and interaction operator 512 equals to the sum of the external sources 513 and scattering sources 514. The leakage operator 511 defines the net particle out-flow from the volume; the interaction operator 512 defines the rate of particles interacting with media, such as by absorption or scattering; the external sources 513 define the sum of the particles from non-scattering sources, such as the x-ray source; and the scattering sources 514 define the particles scattering into the phase space.

With respect to the mathematic equation in the BTE 510, the variable r denotes to a photon's spatial coordinates, the variable E denotes to a photon's energy, and the variable $\Omega$ denotes a photon's streaming direction. Further, $\mu_t$ denotes the linear attenuation coefficient (which describes how easily a voxel can be penetrated by the photon), S denotes an external source of photons, and $\psi$ defines the photon fluence (or angular flux) described over spatial coordinates r, energy E and streaming direction $\Omega$. In other words, the "photon fluence" or "angular flux" is the sum of photon track lengths per unit volume and unit time in direction $\Omega$ at point r. Combined with known quantities such as the linear attenuation coefficient (the probability that a photon will interact per unit track length) or kerma (the energy released by photons interacting with the object), the photon fluence may be used to derive physically-measurable quantities such as radiation dose rate.

As shown by the segmented volume 520 of FIG. 5, during the above multiple iterations of simulation, the dose-distribution-calculation module 240 may track the macroscopic behaviour of photons passing through the voxels of the segmented volume 520. Taking the voxel 521 as an example, the dose-distribution-calculation module 240 may record that some photons passed through, some were absorbed by, and some scattered in, the voxel 521 during simulation. Thus, the dose-distribution-calculation module 240 may apply those photons' macroscopic behaviour values to the respective coordination variable r, energy variable E, and directional variable Ω in the BTE 510. The dose-distribution-calculation module 240 may supply voxel 521's material type and density as the values for $\mu_t$, and provide the photons' primary source as well as the scattering sources identified during simulation to the BTE 510.

The dose-distribution-calculation module 240 may collect the respective macroscopic behaviour information for each of the voxels in the segmented volume 520 during every iteration of simulation. After inputting all relevant information into the BTE 510, the dose-distribution-calculation module 240 may solve the BTE 510 by generating the solution $\psi$, which shows a 3D distribution of the photon fluence among all the voxels in the segmented volume 520. The 3D photon fluence distributions among all the voxels may then be stored in a dose distribution map 530. Thus, the dose distribution map 530 may provide a corresponding 3D photon fluence distribution value for each of the voxels in the segmented volume 520.

In some embodiments, the dose-distribution-calculation module 240 may utilize a "Monte Carlo method" solver or a "deterministic method" solver to calculate the photon fluence solution to the BTE 510. Monte Carlo method solver may converge to the solution by increasing the number of photons simulated (stochastic convergence), while the deterministic method solver may converge to the solution by refining the angular, spatial or energy mesh resolution (deterministic convergence). The run time of the deterministic method solver is weakly dependent on the number of view angles simulated, making it well-suited for CT dose calculations. Thus, the dose-distribution-calculation module 240 may select the deterministic method solvers for solving the BTE 510 for its advances in computationally efficiency and in allowing rapid and accurate dose calculations on desktop computers.

In some embodiments, the dose-distribution-calculation module 240 may refine the discretized variables or adjust the parameters of the BTE solver, in order to optimize the BTE solver's accuracy and minimize its run times. For example, the BTE solver parameters that can be optimized include voxel size, energy grouping scheme, angular discretization, and scattering source representation. These parameters may be further adjusted to account for commercial CT scanner's helical trajectories, the source spectrum (including heel effect), variable collimation, bowtie filtration, and tube current modulation.

Referring back to FIG. 2, based on the dose distribution map 245 generated by the dose-distribution-calculation module 240 and the segmented volume 225 provided by the auto-segmentation module 220, the dose-tabulation module 250 may be configured to generate a patient-specific organ dose 140 for an organ-of-interest. The patient-specific organ dose 140 may be used to show an amount of radiation dose the organ-of-interest was exposed to during a CT scanning operation.

Figure 6:
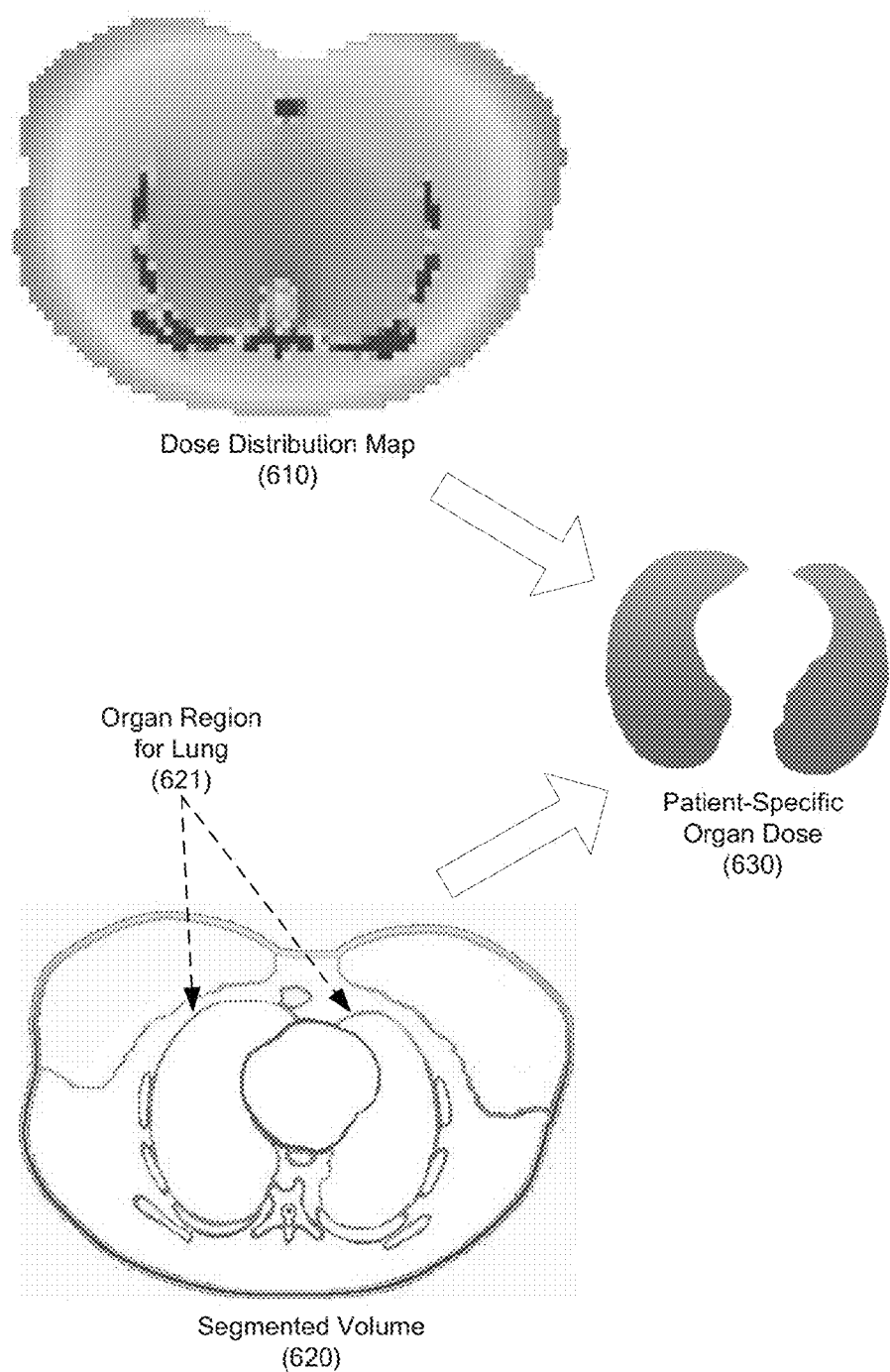
FIG. 6 illustrates a dose tabulation approach to generate a patient-specific organ dose.

FIG. 6 illustrates a dose tabulation approach to generate a patient-specific organ dose, in accordance with certain embodiments of the present disclosure. In FIG. 6, the organ-of-interest may be a patient's lung. The dose-tabulation module of FIG. 2 may generate a patient-specific organ dose 630 based on the dose distribution map 610 and the segmented volume 620. Specifically, the dose-tabulation module may identify the organ region for lung 621 in the segmented volume 620 that corresponds to the organ-of-interest, and extract a subset of voxels from the segmented volume 620 that are associated with the lung organ region 621. The subset of voxels associated with the lung organ region 621 may be those voxels in segmented volume 620 that are within the contoured boundaries of the lung organ region 621. Afterward, the dose-tabulation module may collect the photon fluence distribution values associated with the subset of voxels from the dose distribution map 610, and tabulate these photon fluence distribution values into a "lung photon fluence" value for the organ-of-interest lung. Finally, the dose-tabulation module may convert the lung photon fluence to the patient-specific organ dose 630 (in mGy).

In some embodiments, the dose-tabulation module may also compute an "average organ dose" by dividing the patient-specific organ dose 630 by the organ-of-interest' mass. For an organ region that is completely contained in the segmented volume 620, the dose-tabulation module may calculate the organ mass by tabulating the densities of the subset of voxels defined in a material density map. For an organ region that extends beyond the segmented volume, the organ volume may be estimated based on density values from a whole-body expert case.

Figure 7:
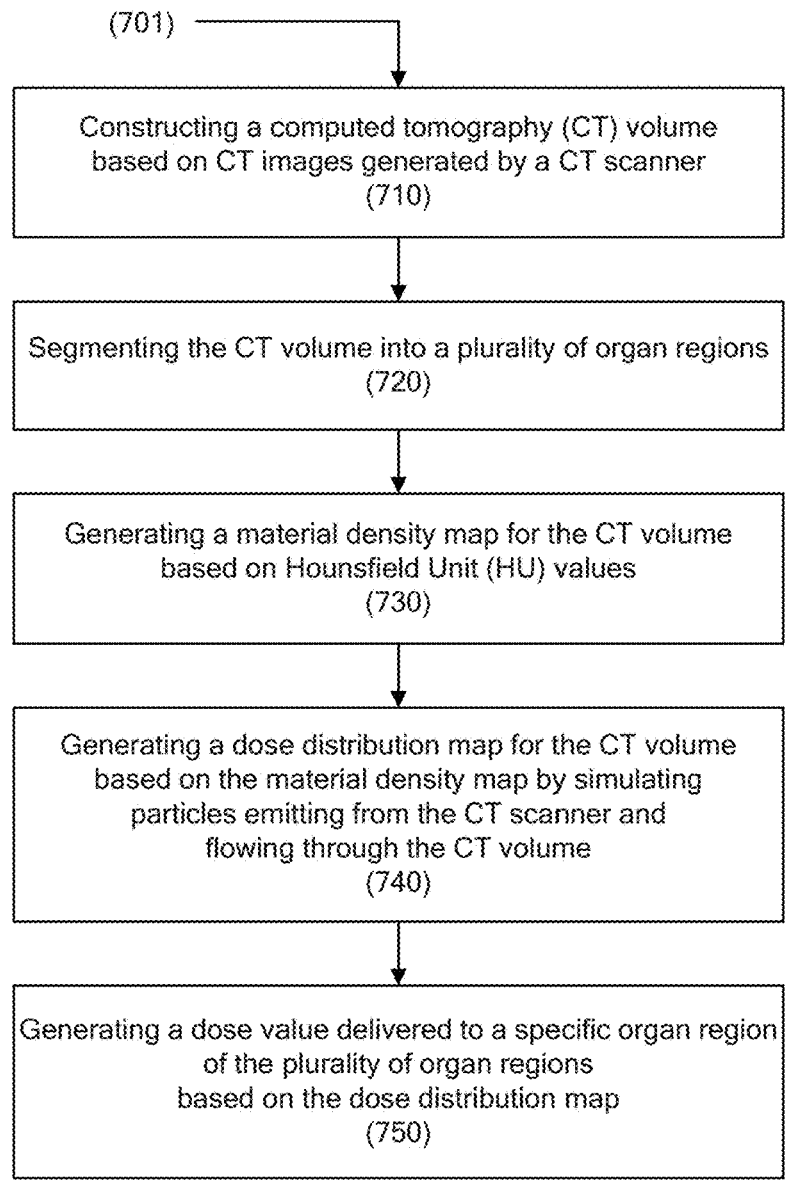
FIG. 7 shows a flow diagram illustrating one embodiment of a process for providing automatic patient-specific organ dose-estimation, all in accordance with certain embodiments of the present disclosure.

FIG. 7 shows a flow diagram illustrating one embodiment of a process for providing automatic patient-specific organ dose-estimation, according to certain embodiments of the present disclosure. One example process 701 sets forth various functional blocks or actions that may be described as processing steps, functional operations, events, and/or acts, which may be performed by hardware, software, and/or firmware. Those skilled in the art in light of the present disclosure will recognize that numerous alternatives to the functional blocks shown in FIG. 7 may be practiced in various implementations. In some embodiments, machine-executable instructions for the process 701 may be stored in memory, executed by a processing unit, and/or implemented in a dose-estimation system, such as the dose-estimation system 130 of FIG. 1.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments. Moreover, one or more of the outlined steps and operations may be performed in parallel.

At block 710, the dose-estimation system may construct a CT volume based on CT images generated by a CT scanner. In some embodiments, the CT scanner may be a cone-beam CT scanner, and the CT volume may be a cone-beam CT volume constructed based on a plurality of x-ray projections generated by the CT scanner. Further, the particles emitting from the CT scanner may be x-ray photons originated from a plurality of x-ray projection sources.

At block 720, the dose-estimation system may segment the CT volume into a plurality of organ regions. The dose-estimation system may first partition the CT volume into a plurality of voxels. Each of the plurality of organ regions may contain a subset of voxels selected from the plurality of voxels. In some embodiments, the dose-estimation system may segment the CT volume by identifying the plurality of organ regions in the CT volume based on the plurality of voxels' HU values. Alternatively, the dose-estimation system may segment the CT volume by identifying the plurality of organ regions in the CT volume based on an atlas which contains previously-segmented organ regions associated with a previous CT volume. Further, the dose-estimation system may perform a deformable registration operation to map the previously-segmented organ regions in the previous CT volume to the plurality of organ regions in the CT volume.

At block 730, the dose-estimation system may generate a material density map for the CT volume based on the plurality of voxels' HU values. The material density map may be used to define a corresponding material type and density for each of the plurality of voxels in the CT volume.

At block 740, the dose-estimation system may generate a dose distribution map for the CT volume based on the material density map by simulating particles emitting from the CT scanner and flowing through the plurality of voxels. The dose distribution map may store a plurality of 3D particle fluence distribution values among the plurality of voxels. In some embodiments, the dose-estimation system may simulate the CT scanner based on the CT scanner's configuration. The CT scanner's configuration may account for beam energy (kVp), beam current (mA), exposure time, collimation, and/or beam filtering as a function of gantry angle and patient position. Further, the dose-estimation system may simulate the CT scanner by using a fluence grid associated with the CT scanner to provide a spatially-dependent particle fluence and energy spectra for the particles.

In some embodiments, the dose-estimation system may simulate macroscopic behavior of the particles emitting from the CT scanner and flowing through the plurality of voxels. The dose-estimation system may simulate the particles being absorbed or scattered in the plurality of voxels. The dose-estimation system may simulate the transporting of the particles emitting from the CT scanner through the plurality of voxels to calculate a set of scattering sources. The dose-estimation system may then simulate the transporting of the particles from the set of scattering sources across the plurality of voxels to calculate angular flux in the plurality of voxels. Further, the dose-estimation system may simulate iterating through the transporting of the particles until a converged solution is obtained in calculating angular flux in the plurality of voxels.

In some embodiments, the dose-estimation system may construct a BTE using the macroscopic behavior of the particles and the material density map. The dose-estimation system may generate the dose distribution map by using a deterministic method to solve the BTE and calculate the 3D particle fluence distribution values among the plurality of voxels. Further, the dose-estimation system may obtain a 3D particle fluence distribution value associated with a specific voxel in the plurality of voxels from the deterministic method's solution, and store the 3D particle fluence distribution value associated with the specific voxel in the dose distribution map.

At block 750, the dose-estimation system may generate a dose value delivered to a specific organ region of the plurality of organ regions, based on the subset of voxels associated with the specific organ region and the subset of voxels' 3D particle fluence distribution values stored in the dose distribution map. Specifically, the dose-estimation system may identify from the plurality of voxels the subset of voxels that are associated with the specific organ region, and generate the organ dose value by accumulating corresponding dose values for the subset of voxels from the dose distribution map.

Thus, methods and systems for providing automatic patient-specific organ dose-estimation have been described. The techniques introduced above can be implemented in special-purpose hardwired circuitry, in software and/or firmware in conjunction with programmable circuitry, or in a combination thereof. Special-purpose hardwired circuitry may be in the form of, for example, one or more application-specific integrated circuits (ASICs), programmable logic devices (PLDs), field-programmable gate arrays (FPGAs), and others.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. Those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

Software and/or firmware to implement the techniques introduced here may be stored on a non-transitory machine-readable storage medium and may be executed by one or more general-purpose or special-purpose programmable microprocessors. A "machine-readable storage medium", as the term is used herein, includes any mechanism that provides (i.e., stores and/or transmits) information in a form accessible by a machine (e.g., a computer, network device, personal digital assistant (PDA), mobile device, manufacturing tool, any device with a set of one or more processors, etc.). For example, a machine-accessible storage medium includes recordable/non-recordable media (e.g., read-only memory (ROM), random access memory (RAM), magnetic disk storage media, optical storage media, flash memory devices, etc.)

Although the present disclosure has been described with reference to specific exemplary embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense.

We claim:

1. A method for calculating a patient-specific organ dose, comprising:
   constructing a computed tomography (CT) volume based on CT images generated by a CT scanner;
   segmenting the CT volume into a plurality of organ regions, wherein the CT volume contains a plurality of voxels, and each of the plurality of organ regions contains a subset of voxels selected from the plurality of voxels;

generating a material density map for the CT volume based on the plurality of voxels' Hounsfield Unit (HU) values, wherein the material density map defines a corresponding material type and density for each of the plurality of voxels;

generating a dose distribution map for the CT volume based on the material density map by simulating the CT scanner based on the CT scanner's configuration, simulating macroscopic behavior of particles emitting from the CT scanner and flowing through the plurality of voxels, and constructing a Boltzmann Transport Equation (BTE) using the macroscopic behavior of the particles and the material density map, wherein the dose distribution map stores a plurality of three-dimensional (3D) particle fluence distribution values among the plurality of voxels; and generating a dose value delivered to a specific organ region of the plurality of organ regions based on the dose distribution map.

2. The method as recited in claim 1, wherein the segmenting of the CT volume into the plurality of organ regions comprising:
identifying the plurality of organ regions in the CT volume based on the plurality of voxels' HU values.

3. The method as recited in claim 1, wherein the segmenting of the CT volume into the plurality of organ regions comprising:
identifying the plurality of organ regions in the CT volume based on an atlas which contains previously-segmented organ regions associated with a previous CT volume.

4. The method as recited in claim 3, wherein the segmenting of the CT volume into the plurality of organ regions further comprising:
performing a deformable registration operation to map the previously-segmented organ regions in the previous CT volume to the plurality of organ regions in the CT volume.

5. The method as recited in claim 1, wherein the simulating of the CT scanner comprising:
using a fluence grid associated with the CT scanner to provide a spatially-dependent particle fluence and energy spectra for the particles.

6. The method as recited in claim 1, wherein the CT scanner's configuration accounts for beam energy (kVp), beam current (mA), exposure time, collimation, and/or beam filtering as a function of gantry angle and patient position.

7. The method as recited in claim 1, wherein the simulating of the macroscopic behavior of particles emitting from the CT scanner comprising:
simulating the particles being absorbed or scattered in the plurality of voxels.

8. The method as recited in claim 7, wherein the simulating of the macroscopic behavior of particles emitting from the CT scanner further comprising:
transporting the particles emitting from the CT scanner through the plurality of voxels to calculate a set of scattering sources.

9. The method as recited in claim 8, wherein the simulating of the macroscopic behavior of particles emitting from the CT scanner further comprising:
transporting the particles from the set of scattering sources across the plurality of voxels to calculate angular flux in the plurality of voxels.

10. The method as recited in claim 9, wherein the simulating of the macroscopic behavior of particles emitting from the CT scanner further comprising:
iterating through the transporting of the particles until a converged solution is obtained in calculating the angular flux in the plurality of voxels.

11. The method as recited in claim 1, wherein the generating of the dose distribution map further comprising:
generating the dose distribution map by using a deterministic method to solve the BTE and calculate the 3D particle fluence distribution values among the plurality of voxels.

12. The method as recited in claim 11, wherein the generating of the dose distribution map further comprising:
obtaining a 3D particle fluence distribution value associated with a specific voxel in the plurality of voxels from the deterministic method's solution; and
storing the 3D particle fluence distribution value associated with the specific voxel in the dose distribution map.

13. The method as recited in claim 1, wherein the generating of the dose value delivered to the specific organ region comprising:
generating the organ dose value by accumulating corresponding dose values for the subset of voxels from the dose distribution map and based on the 3D particle fluence distribution values for the subset of voxels stored in the dose distribution map.

14. The method as recited in claim 1, wherein the CT scanner is a cone-beam CT scanner and the CT volume is a cone-beam CT volume constructed based on a plurality of x-ray projections generated by the CT scanner.

15. The method as recited in claim 1, wherein the particles emitting from the CT scanner are x-ray photons originated from a plurality of x-ray projection sources.

16. A method for calculating patient-specific organ dose, comprising:
segmenting a computed tomography (CT) volume originated from a CT scanner into a plurality of organ regions, wherein the CT volume contains a plurality of voxels, and each of the plurality of organ regions contains a subset of voxels selected from the plurality of voxels;
determining material types and densities for the plurality of voxels in the CT volume based on the plurality of voxels' Hounsfield Unit (HU) value;
generating a dose distribution map for the CT volume by simulating macroscopic behavior of particles emitting from the CT scanner and flowing through the plurality of voxels and performing a Boltzmann Transport Equation (BTE) calculation with a deterministic solver based on the macroscopic behavior of the particles, the CT scanner's configuration, and the plurality of voxels' material types and densities, wherein the dose distribution map stores a plurality of dose values associated with the plurality of voxels; and
generating a dose value for a specific organ region selected from the plurality of organ regions, based on the subset of voxels associated with the specific organ region and the subset of voxels' dose values stored in the dose distribution map.

17. The method as recited in claim 16, wherein the segmenting of the CT volume into the plurality of organ regions comprising:

identifying the plurality of organ regions in the CT volume based on an atlas which contains previously-segmented organ regions associated with a previous CT volume.

18. The method as recited in claim 17, wherein the segmenting of the CT volume into the plurality of organ regions further comprising:
performing a deformable registration operation to map the previously-segmented organ regions in the previous CT volume to the plurality of organ regions in the CT volume.

19. The method as recited in claim 16, wherein the performing the BTE calculation with the deterministic solver comprising:
obtaining a 3D particle fluence distribution value associated with a specific voxel in the plurality of voxels from the deterministic solver's solution; and
storing the 3D particle fluence distribution value associated with the specific voxel in the dose distribution map.

20. A system configured to calculate patient-specific organ dose, comprising:
a memory system containing a set of instructions; and
a processor, coupled to the memory system, wherein in response to execution of the set of instructions by the processor, causes the processor to:
segment a computed tomography (CT) volume into a plurality of organ regions, wherein the CT volume is constructed based on CT images generated by a CT scanner, the CT volume contains a plurality of voxels, and each of the plurality of organ regions contains a subset of voxels selected from the plurality of voxels;
generate a material density map for the CT volume based on the plurality of voxels' Hounsfield Unit (HU) values, and the material density map defines a corresponding material type and density for each of the plurality of voxels;
generate a dose distribution map for the CT volume based on the material density map by simulating macroscopic behavior of particles emitting from the CT scanner and flowing through and being absorbed or scattered in the plurality of voxels, and the dose distribution map stores a plurality of 3-dimension (3D) particle fluence distribution values among the plurality of voxels, wherein the simulating the macroscopic behavior of the particles further comprises:
transporting the particles emitting from the CT scanner through the plurality of voxels to calculate a set of scattering sources; and
transporting the particles emitting from the set of scatting sources across the plurality of voxels to calculate angular flux in the plurality of voxels; and
generate a dose value delivered to a specific organ region of the plurality of organ regions, based on the dose distribution map.

21. The system as recited in claim 20, wherein the processor is configured to simulate the macroscopic behavior of the particles emitting from the CT scanner and flowing through the plurality of voxels by further iterating through the transporting of the particles until a converged solution is obtained in calculating the angular flux in the plurality of voxels.

22. The system as recited in claim 20, wherein the processor is configured to generate the dose distribution map by:
constructing a Boltzmann Transport Equation (BTE) using the simulated macroscopic behavior of the particles and the material density map; and
using a deterministic method to solve the BTE and calculate the3D particle fluence distribution values among the plurality of voxels as the dose distribution map.

* * * * *